United States Patent

Tatar

[19]

[11] Patent Number: 5,910,142
[45] Date of Patent: Jun. 8, 1999

[54] POLYAXIAL PEDICLE SCREW HAVING A ROD CLAMPING SPLIT FERRULE COUPLING ELEMENT

[75] Inventor: Stephen Tatar, Montvale, N.J.

[73] Assignee: Bones Consulting, LLC, Summit, N.J.

[21] Appl. No.: 09/174,962

[22] Filed: Oct. 19, 1998

[51] Int. Cl.⁶ .................................................. A61B 17/70
[52] U.S. Cl. .................. 606/61; 606/72; 606/73
[58] Field of Search .................. 606/60, 61, 69, 606/70, 72, 73, 75

[56] References Cited

U.S. PATENT DOCUMENTS

| | | | |
|---|---|---|---|
| 5,207,678 | 5/1993 | Harms et al. | 606/61 |
| 5,716,356 | 2/1998 | Biedermann et al. | 606/61 |
| 5,728,098 | 3/1998 | Sherman et al. | 606/61 |
| 5,733,286 | 3/1998 | Errico et al. | 606/61 |
| 5,782,833 | 7/1998 | Haider | 606/61 |
| 5,797,911 | 8/1998 | Sherman et al. | 606/61 |
| 5,810,819 | 9/1998 | Errico et al. | 606/61 |

*Primary Examiner*—Michael Buiz
*Assistant Examiner*—Daphna Shai
*Attorney, Agent, or Firm*—Joseph P. Errico, Esq

[57] ABSTRACT

A polyaxial pedicle screw device for use with rod implant apparatus, which utilizes a rod mounted ferrule, includes a screw having a curvate head and a rod receiving body. The body has a rod receiving channel and an axial bore into which the head of the screw is inserted. The interior surface of the bore is inwardly curvate at the lower end thereof to form a socket for polyaxially retaining the curvate head of the screw. In an initial position the screw head remains polyaxially free with respect to the body. The rod mounted ferrule seats into a small curvate recess in the upper portion of the screw head such that the rod may enter the body at a variety of angles while maintaining a secure seating against the head of the screw. The insertion of a top set screw compresses down on the ferrule, locking the rod in position, and onto the screw head, locking it and the body in position, thus completely securing the assembly.

4 Claims, 2 Drawing Sheets

POLYAXIAL PEDICLE SCREW HAVING A ROD CLAMPING SPLIT FERRULE COUPLING ELEMENT

BACKGROUND OF THE INVENTION

1. Field of the Invention

This invention relates generally to a pedicle screw having polyaxial rod coupling means for use with orthopedic fixation systems. More particularly, the present invention relates to a screw assembly for use in the immobilization of a sequence of spinal bones, including a threaded screw element and coupling mechanism for polyaxially aligning and mounting a rod within a top body portion of the screw.

2. Description of the Prior Art

The spinal column is highly complex system of bones and connective tissues which houses and protects critical elements of the nervous system and the arterial and venous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. The present invention relates to spinal fixation devices for immobilizing and altering the alignment of the spine over a large number, for example more than three or four, vertebra by means of affixing at least one elongate rod to the sequence of selected bones.

Such "rod assemblies" generally comprise a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape.

It has been identified, however, that a considerable difficulty is associated with inserting screws along a misaligned curvature and simultaneously exactly positioning the coupling elements such that the receiving loci thereof are aligned so that the rod can be passed therethrough without distorting the screws. Attempts at achieving proper alignment with fixed screws is understood to require considerably longer operating time, which is known to increase the incidence of complications associated with surgery. Often such alignments, with such fixed axes devices could not be achieved, and the entire instrumentationing effort would end unsuccessfully.

In addition, for many patients specific pathology it is desirable that the rod extend down into and beyond the lumbar portion of the spine, and for the end of the rod to be coupled to the sacral bone. Providing such an end to the assembly in the sacral bone has been understandably suggested inasmuch as it provides superior support to the full extent of the assembly. The most suitable position for the insertion of the screws into the sacral body may not, however, conform to the direction extent of the rod as it is affixed to the entirety of the assembly. Misalignment of the rod with respect to the screw and the coupling element is often a source of considerable disadvantage for the surgeon, often requiring considerable efforts to be expended bending and aligning the rod with the receiving locus of the coupling element. These additional efforts are a considerable difficulty associated with the proper and expeditious affixation, and over the long term, the offset of the rod can have a deleterious effect on the overall performance of the entire implantation assembly.

The art contains a variety of attempts at providing instrumentation which permit a freedom with respect to angulation of the screw and the coupling element. These teachings, however, have generally been complex, and inadequately reliable with respect to durability. The considerable drawbacks associated with the prior art systems include complexity, difficulty properly positioned the rod and coupling elements, and the tedious manipulation of the many parts associated with the complex devices.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more dearly understood in conjunction with the descriptions of the preferred embodiments disclosed hereafter.

SUMMARY OF THE INVENTION

The preceding objects of the invention are achieved by the present invention which is a bone screw for connecting a bone with a rod, said bone screw comprising: a screw member having a threaded portion and a head, said head having a spherical segment-shaped portion and a recess formed therein; a cylindrical receiver member for receiving said head of said screw member and said rod, said receiver member having a first end and a second end, a bore provided in said receiver member between said first and second ends, a hollow spherical portion in said bore for receiving said head at a position inwards of said second end, said receiver member further having a substantially U-shaped cross-section with two free legs which are provided with a thread; a pressure means mounted to a the rod and initially selectably advanceable therealong, said pressure means being positionable in the recess of the head, and said pressure means being lockable to the rod when a radial force is applied thereto; and a locking means screwed onto said receiver member thread for providing a radial force onto the pressure means thereby locking it to the rod, and for forcing the pressure means onto the head of the screw, thereby locking the body, rod and screw together.

More particularly, the present invention comprises a bone screw having a curvate head, a rod receiving body having an axial bore and tapered bottom interior end for receiving and polyaxially retaining the curvate head of the screw, a slotted ferrule which is mounted around the rod and which has a curvate outer surface for seating on the head of the screw, and a compression nut which drives the assembly into a compression locked configuration.

More specifically, the screw comprises a threaded shaft for insertion into the bone and a curvate head. The curvate head of the screw has a lower half which is integrally formed with the shaft, and otherwise comprises spherical section which is less than a full hemisphere. The upper half of the head is flattened having a recess formed in the axial center thereof, for receiving a screw driving tool (so the screw may be driven into the bone). This recess has a rounded concave lip conformation for receiving thereon, the curvate outer surface of the split ferrule which is mounted around the rod.

The rod receiving body portion comprises a tubular section having an axial bore and a axially transverse channel formed in the sides thereof, into which a rod may be received. The bottom portion of the axial bore is inwardly tapered such that the curvature of the taper is substantially equivalent to the curvature of the lower portion of the screw head, i.e. a constant radius of curvature. The diameter of the shaft of the screw at its interface with the head is more narrow than the bottom opening in the body portion such that, when the head is seated in the bottom of the coupling element, the screw and coupling element may polyaxially rotate relative to one another.

A split ferrule, which comprises a compressible ring, is mounted around the rod such that the rod extends through the ring and the ring may slide axially along the rod. A compressive force applied to the ferrule, across the split therein, however, causes the diameter of the ferrule to contract and compressibly lock onto the rod. It shall be understood that the inner surface of the split ferrule is cylindrical (having a defined and axially constant diameter—but for the circumferential discontinuity).

More particularly, the exterior surface of the ferrule comprises a curvate conformation, such that the ferrule's exterior resembles the outer portion of a toroid. With more geometric specificity, the ferrule is sphere having had a concentric cylindrical section removed therefrom such that it may receive a rod therethrough, and a radial slot formed therein, such that the ferrule is compressible into a smaller diameter conformation.

The curvate exterior of the split ferrule, when mounted about the rod, permits the rod to seat solidly against an object having a concave conformation (for example, the curvate lip of the recess in the upper surface of the head of the screw) and to maintain a stable contact point thereon while the rod is angulated through a range of orientations. Equally important is the ability of the ferrule to receive a downward load thereonto as the rod is positioned in different orientations. It is this downwardly directed loading which causes the ferrule to close about the rod and tightly lock the assembly together.

The present invention may be assembled and utilized in the following manner. The screw shaft is inserted downwardly, through the axial bore of the body portion, until the curvate lower portion of the head nests in the lower curvately tapered socket of the body. The screw is then inserted into the appropriate portion of the spinal bone. The body portion is then polyaxially rotated relative to the fixed orientation of the screw head. The split ferrule is then mounted around the rod in an undeflected state and may be translated along the rod into a desired axial position. The rod and the ferrule are then inserted into the body portion of the screw assembly, this step of mating and insertion of the rod into the body being substantially enhanced by the polyaxial rotation of the body relative to the screw. The ferrule is then positioned so that it seats against the head of the screw, and more specifically against the curvate lip of the recess in the upper portion of the head of the screw. The relative geometries of the assembly, and specifically the ferrule, rod, and screw head permit the rod to angulate relative to the body without disrupting the solid contact of the ferrule against the head of the screw, independent of the screw head's orientation relative to the body. This flexibility in proper assembly orientation provides tremendous ease of use, and corresponding time of implantation, advantages for the surgeon in constructing the assembly in the operative field.

A nut, set screw, or other device for securing the rod and ferrule in the channel of the body, and for providing a compressive force against the ferrule is also provided. This securing device is brought to bear against the upper surface of the ferrule, thus causing the ferrule to be compressed between the head of the screw and the securing device. This causes the ferrule to contract and lock the rod in place (axially and at the desired angle relative to the body). The compressive force against the ferrule is further transferred to the head of the screw, which is compression locked to the curvate interior surface of the body portion.

Multiple screw and coupling element assemblies are generally necessary to complete the full array of anchoring sites for the rod immobilization system, however, the screw and coupling element assembly of the present invention is designed to be compatible with alternative rod systems (using ferrules or not) so that where necessary, the present invention may be employed to rectify the inadequacies of other rod implant systems.

BRIEF DESCRIPTION OF THE FIGURES

The following detailed description of the preferred embodiment is provided with reference to the following Figures.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
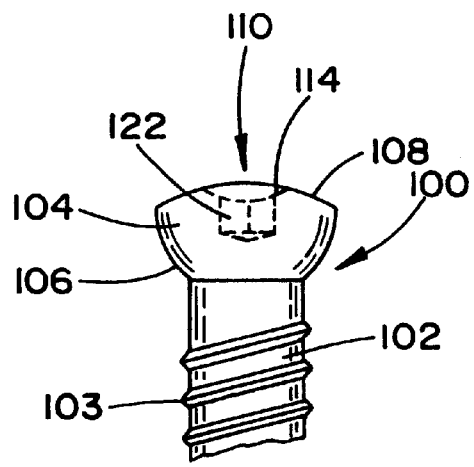
FIG. 1 is a side view of a screw having a curvate head which is an aspect of the present invention.

Referring now to FIG. 1, a side view of the screw portion of the present invention, comprising a threaded shaft and a partially curvate head, is shown. The screw 100 comprises a threaded shaft 102, the threading 103 itself may be selected from the varieties of thread designs (i.e., pitch, grip, inclination, etc.) which are best suited for gripping bone. The curvate head 104 includes a constant radius of curvature lower portion 106 which is convex and therefore defines a partial hemispherical section. The curvate head 104 is integrally formed at the top of the shaft 102. The upper portion 108 of the curvate head 104 includes a recess 110. The recess 110 is bifunctional insofar as it includes a slot 112 or other suitable screw driving tool receiving conformation as well as a curvately concave circumferential lip 114. It is preferably that this concave lip have a constant radius of curvature.

Figure 2:
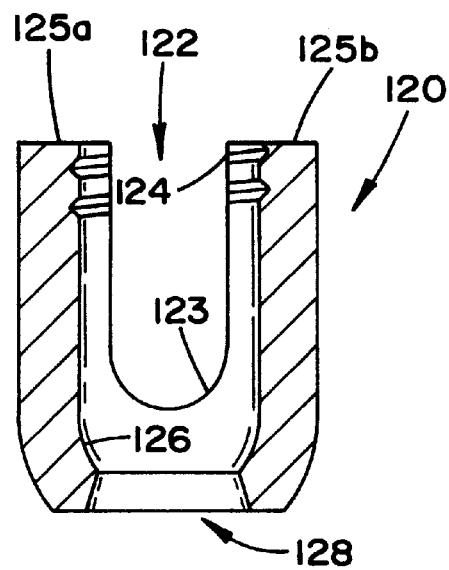
FIG. 2 is a side cross-section view of the body portion of present invention.

Referring now to FIG. 2, the body element 120 is provided in a side cross-section view. The body 120 is generally cylindrical and has an axial bore 122 extending therethrough. The body includes a channel 123 for receiving a rod 150 therethrough, the channel dividing the upper portion of the body into a pair of upwardly extending members 125a, 125b. The interior of the top portion of the bore (the upwardly extending members 125a, 125b) includes a threading 124 (which threading may alternatively—or additionally—be provided on the outer upper surface of the body) for receiving a set screw (or locking nut). The lower portion of the axial bore 122 includes a curvate taper 126 which forms a socket, preferably having the identical radius of curvature of the curvature of the lower half 106 of the screw 100. The bottom opening 128 of the axial bore 122 is larger than the shaft 102 of the screw 100, but is less than the diameter of the head 104, so that the head can be nested in the socket 126 at the bottom of the bore 122, with the undersurface 106 of the head 104 slidably (initially) nested against the tapered interior surface 126. The corresponding geometries permit the screw 100 to polyaxially rotate relative to the body 120 without disrupting the overall nesting of the head 104 in the socket 126.

Figure 3:
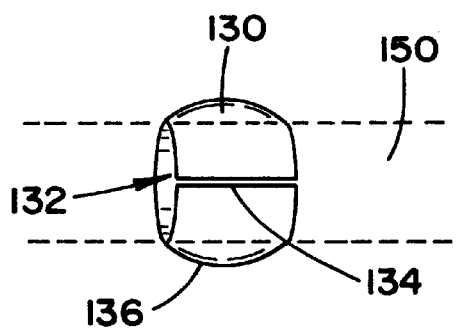
FIG. 3 is a side perspective view of the split ferrule of the present invention, wherein the rod around which it seats is provided in phantom to illustrate its intended mounting orientation.

Referring now to FIG. 3, the ferrule 130 of the present invention is shown in a side perspective view with the rod 150 of the implant assembly shown extending through the ferrule in phantom. More particularly, the ferrule 130 comprises a spherical element having a concentric cylindrical section removed therefrom, forming a cylindrical bore 132 through the element which can therefore receive the rod 150. The ferrule 130 further includes a slot 134 formed therein, which extends fully through the exterior into the central bore 132. This slot 134 permits the ferrule to expand and contract about the rod 150 upon the application of a corresponding radial load. In an undeflected state, the ferrule 130 seats around the rod 150 snugly, but can be manually translated axially along the rod. In a compressed state, the inner surface of the central bore 132 is crushed against the rod surface, thereby preventing translation along the rod.

The exterior surface 136 of the ferrule 130 is curvate, having a constant radius of curvature. This conformation provides the ability to snugly nest the ferrule 130 into the concave curvate lip 114 of the recess 100 in the head 104 of the screw 100. Because the exterior of the ferrule 130 and the lip of the recess 114 are each designed with similar constant radii of curvature, the ferrule 130 initially may rotate and slide relative to the screw 100, thereby permitting the screw 100 and the rod 150 to rotate relative to one another through perpendicular orientations to skewed orientations. This mobility provides for ease of insertion of the rod 150 into the body 120 as the rod 150 needs not be perfectly positioned in order to provide a perfect seating of the ferrule 130 against the screw head 104.

Figure 4:
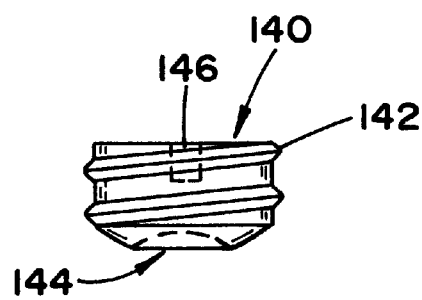
FIG. 4 is a side view of a set screw of the present invention.

Referring now to FIG. 4, the set screw 140 of the present invention is provided in a side cross-section view. The set screw 140 has a cylindrical body having a threading 142 thereon. The threading 142, and the diameter of the set screw 140 itself, are designed to seat in the axial bore 122 of the body 120 and mate the threading 124 therein. (It shall be understood that the set screw 140 is replaced—or complemented—by a locking nut in the embodiment of the present invention wherein a threading is provided on the exterior surface of the body 120). The set screw further includes a concave underside 144 which is ideally suited for seating against the curvate exterior surface of the ferrule 130. The upper portion of the set screw includes a recess 146 into which a screw driving tool may be inserted to drive the set screw into the coupling element.

Figure 5:
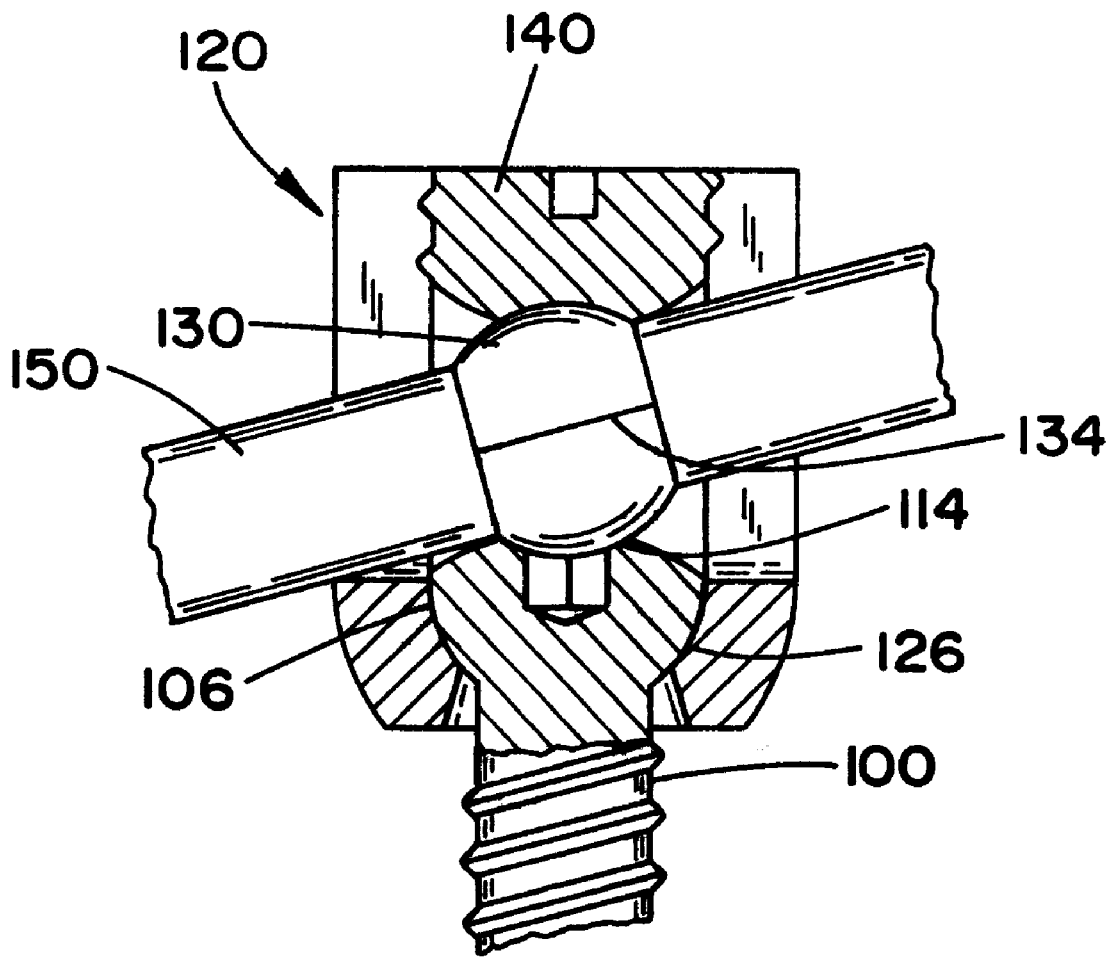
FIG. 5 is a side cross-sectional view of the present invention in its fully assembled disposition having a rod securely locked therein.

Referring now also to FIG. 5, in which the entire assembly has been locked together with a rod 150 in the channel 123 of the body 120, the complete assembly and function of the invention is set forth herein below. Once the screw 100 and the body 120 have been assembled by advancing the screw through the axial bore until the head of the screw seats in the socket of the body, and the shaft of the screw extends out from the bottom of the body, the surgeon may drive the screw shaft into the spinal bone of the patient. At this time, the body 120 and the screw head may rotate freely relative to one another, being constrained only by the shaft 102 of the screw 100 contacting the perimeter surface of the bottom opening of the bore 126 at the extreme range of the allowed rotation.

Once the surgeon has properly positioned the body 120, the rod 150 and ferrule 130 are placed in the channel 123 of the body 120, and seated against the curvate concave lip 114 in the top of the screw 120. This permits the rod to be received in the body without requiring absolute perpendicularity of the screw with the rod, nor between the axial bore and the rod. The subsequent insertion and tightening of the set screw 140 downward onto the ferrule 130 causes the slot in the ferrule 130 to compress and lock the ferrule to the rod, and the ferrule to compress against the head 104 of the screw 100. The head of the screw is in turn compressed against the inner surface of the socket of the body, and to be securely locked together. Thus, complete insertion of the set screw into the axial bore causes the crush locking of the entire assembly, independent (within a range) of the angle the body 120 to the screw 100 or the rod 150.

While there has been described and illustrated embodiments of a polyaxial screw and ferruled rod assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A bone screw for connecting a bone with a rod, said bone screw comprising a screw member having a threaded portion and a head, said head having a spherical segment-shaped portion and a recess formed therein, a cylindrical receiver member for receiving said head of said screw member and said rod, said receiver member having a first end and a second end, a bore provided in said receiver member between said first and second ends, a hollow spherical portion in said bore for receiving said head at a position inwards of said second end, said receiver member further having a substantially U-shaped cross-section with two free legs which are provided with a thread, a pressure means mounted to the rod and initially selectably advanceable therealong, said pressure means being positionable in the recess of the head, and said pressure means being lockable to the rod when a radial force is applied thereto, and a locking means screwed onto said receiver member thread for providing a radial force onto the pressure means thereby locking it to the rod, and for forcing the pressure means onto the head of the screw, thereby locking the body, rod and screw together.

2. The assembly as set forth in claim 1, wherein the locking means comprises a set screw.

3. The assembly as set forth in claim 1, wherein said locking means comprises a top locking nut.

4. An orthopedic rod implantation apparatus, comprising:

at least one elongate rod;

at least one screw having a threaded portion and a head, said head having a spherical segment-shaped portion and a recess formed therein;

a cylindrical receiver member for receiving said head of said screw member and said rod, said receiver member having a first end and a second end, a bore provided in said receiver member between said first and second ends, a hollow spherical portion in said bore for receiving said head at a position inwards of said second end, said receiver member further having a substantially U-shaped cross-section with two free legs which are provided with a thread;

a pressure means mounted to the rod and initially selectably advanceable therealong, said pressure means being positionable in the recess of the head, and said pressure means being lockable to the rod when a radial force is applied thereto; and a locking means screwed onto said receiver member thread for providing a radial force onto the pressure means thereby locking it to the rod, and for forcing the pressure means onto the head of the screw, thereby locking the body, rod and screw together.

\* \* \* \* \*